US006627593B2

(12) United States Patent
Hei et al.

(10) Patent No.: US 6,627,593 B2
(45) Date of Patent: Sep. 30, 2003

(54) HIGH CONCENTRATION MONOESTER PEROXY DICARBOXYLIC ACID COMPOSITIONS, USE SOLUTIONS, AND METHODS EMPLOYING THEM

(75) Inventors: Robert Dale Hei, Baldwin, WI (US); Thomas Robert Mohs, Eagan, MN (US)

(73) Assignee: Ecolab Inc., St. Paul, MN (US)

( * ) Notice: Subject to any disclaimer, the term of this patent is extended or adjusted under 35 U.S.C. 154(b) by 162 days.

(21) Appl. No.: 09/904,967

(22) Filed: Jul. 13, 2001

(65) Prior Publication Data

US 2003/0087786 A1 May 8, 2003

(51) Int. Cl.[7] .................... C11D 3/395; C07C 409/24; C07C 407/00; A01N 37/16
(52) U.S. Cl. .................. 510/375; 510/376; 510/382; 424/405
(58) Field of Search .................. 510/375, 376, 510/382

(56) References Cited

U.S. PATENT DOCUMENTS

| | | | |
|---|---|---|---|
| 2,512,640 A | 6/1950 | Greenspan et al. |
| 3,122,417 A | 2/1964 | Blaser et al. |
| 3,248,281 A | 4/1966 | Goodenough |
| 3,350,265 A | 10/1967 | Rubinstein et al. |
| 3,514,278 A | 5/1970 | Brink |
| 3,895,116 A | 7/1975 | Herting et al. |
| 3,996,386 A | 12/1976 | Malkki et al. |
| 4,041,149 A | 8/1977 | Gaffar et al. |
| 4,051,058 A | 9/1977 | Böwing et al. |
| 4,051,059 A | 9/1977 | Bowing et al. |
| 4,129,517 A | 12/1978 | Eggensperger et al. |
| 4,191,660 A | 3/1980 | Schreiber et al. |
| 4,244,884 A | 1/1981 | Hutchins et al. |
| 4,370,199 A | 1/1983 | Orndorff |
| 4,404,040 A | 9/1983 | Wang |
| 4,477,438 A | 10/1984 | Willcockson, deceased et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,592,488 A | 6/1986 | Simon et al. |
| 4,613,452 A | 9/1986 | Sanderson |
| 4,655,781 A | 4/1987 | Hsieh et al. |
| 4,715,980 A | 12/1987 | Lopes et al. |
| 4,738,840 A | 4/1988 | Simon et al. |
| 4,802,994 A | 2/1989 | Mouché et al. |
| 4,865,752 A | 9/1989 | Jacobs |
| 4,900,721 A | 2/1990 | Bansemir et al. |
| 4,906,617 A | 3/1990 | Jacquet et al. |

(List continued on next page.)

FOREIGN PATENT DOCUMENTS

| | | |
|---|---|---|
| DE | 35 43 500 A1 | 6/1987 |
| EP | 0 195 619 A2 | 9/1986 |
| EP | 0 233 731 A2 | 8/1987 |
| EP | 0 461 700 A1 | 12/1991 |
| EP | 0 569 066 A1 | 11/1993 |
| EP | 0967203 | 12/1999 |
| EP | 1 061 071 A1 | 12/2000 |
| FR | 2 321 301 A | 3/1977 |
| FR | 2 324 626 A | 4/1977 |
| LU | 78 568 A | 4/1978 |
| WO | WO 95/34537 | 12/1995 |
| WO | WO 98/28267 | 7/1998 |
| WO | WO 00/29038 | 5/2000 |
| WO | WO 01/47359 | 7/2001 |

OTHER PUBLICATIONS

Bell, K. et al., "Reduction of foodborne micro–organisms on beef carcass tissue using acetic acid, sodium bicarbonate, and hydrogen peroxide spray washes", *Food Microbiology*, vol. 14, pp. 439–448 (1997).

Eggensperger, H., "Disinfectants Based on Peracid–Splitting Compounds", *Zbl. Bakt. Hyg.*, I Abt. Orig. B 168, pp. 517–524 (1979).

Lion C. et al., "New decontaminants. Reaction of peroxyacid esters with toxic insecticides", *Bull. Soc. Chim. Belg.*, vol. 100, No. 7, pp. 555–559 (1991).

Merka, V. et al., "Disinfectant properties of some peroxide compounds.", Abstract No. 67542e, *Chemical Abstracts*, vol. 67 (1967).

Mulder, R.W.A.W. et al., "Research Note: Salmonella Decontamination of Broiler Carcasses with Lactic Acid, L–Cysteine, and Hdrogen Peroxide", *Poultry Science*, vol. 66, pp. 1555–1557 (1987).

Parker, W. et al., "Peroxides. II. Preparation, Characterization and Polarographic Behavior of Longchaing Aliphatic Peracids", *Synthesis and Properties of LongChain Aliphatic Peracids*, vol. 77, pp. 4037–4041 (Aug. 5, 1955).

Parker, W. et al., "Peroxides. IV. Aliphatic Diperacids", *Aliphatic Diperacids*, vol. 79, pp. 1929–1931 (Apr. 20, 1957).

Towle, G. et al., "Industrial Gums polysaccharides and Their Derivatives", Second Edition, Ch. XIX, "Pectin", pp. 429–444 (year unknown).

Armak Chemicals, "NEO–FAT Fatty Acids", *Akzo Chemicals Inc.*, Bulletin No. 86–17 (1986).

Computer search results—Level 1—5 patents (Mar. 1994).

Computer search results from Ecolab Information Center (Jun. 1998).

"Emery® Fatty and Dibasic Acids Specifications and Characteristics", *Emery Industries*, Bulletin 145, (Oct. 1983).

Pfizer Chemical Division, "Pfizer Flocon® Biopolymers for Industrial Uses (xanthan broths)", Data Sheet 679, pp. 1–4 (year unknown).

*Primary Examiner*—Yogendra N. Gupta
*Assistant Examiner*—John M Petruncio
(74) *Attorney, Agent, or Firm*—Merchant & Gould P.C.

(57) ABSTRACT

The present invention relates to high concentration compositions of a monoester peroxy dicarboxylic acid, methods employing these high concentration compositions, and methods of making these compositions.

33 Claims, No Drawings

U.S. PATENT DOCUMENTS

| | | | |
|---|---|---|---|
| 4,908,306 A | 3/1990 | Lorincz | |
| 4,917,815 A | 4/1990 | Beilfuss et al. | |
| 4,923,677 A | 5/1990 | Simon et al. | |
| 4,937,066 A | 6/1990 | Vlock | |
| 4,943,414 A | 7/1990 | Jacobs et al. | |
| 4,945,110 A | 7/1990 | Brokken et al. | |
| 4,996,062 A | 2/1991 | Lehtonen et al. | |
| 4,997,571 A | 3/1991 | Roensch et al. | |
| 4,997,625 A | 3/1991 | Simon et al. | |
| 5,004,760 A | 4/1991 | Patton et al. | |
| 5,010,109 A | 4/1991 | Inoi | |
| 5,015,408 A | 5/1991 | Reuss | |
| 5,043,176 A | 8/1991 | Bycroft et al. | |
| 5,069,286 A | 12/1991 | Roensch et al. | |
| 5,084,239 A | 1/1992 | Moulton et al. | |
| 5,093,140 A | 3/1992 | Watanabe | |
| 5,114,178 A | 5/1992 | Baxter | |
| 5,114,718 A | 5/1992 | Damani | |
| 5,122,538 A | 6/1992 | Lokkesmoe et al. | |
| 5,129,824 A | 7/1992 | Keller | |
| 5,130,124 A | 7/1992 | Merianos et al. | |
| 5,139,788 A | 8/1992 | Schmidt | |
| 5,176,899 A | 1/1993 | Montgomery | |
| 5,200,189 A | 4/1993 | Oakes et al. | |
| 5,208,057 A | 5/1993 | Greenley et al. | |
| 5,234,703 A | 8/1993 | Guthery | |
| 5,234,719 A | 8/1993 | Richter et al. | |
| 5,268,003 A | 12/1993 | Coope et al. | |
| 5,292,447 A | 3/1994 | Venturello et al. | |
| 5,314,687 A | 5/1994 | Oakes et al. | |
| 5,336,500 A | 8/1994 | Richter et al. | |
| 5,364,650 A | 11/1994 | Guthery | |
| 5,391,324 A | 2/1995 | Reinhardt et al. | |
| 5,409,713 A | 4/1995 | Lokkesmoe et al. | |
| 5,419,908 A | 5/1995 | Richter et al. | |
| 5,435,808 A | 7/1995 | Holzhauer et al. | |
| 5,436,008 A | 7/1995 | Richter et al. | |
| 5,437,868 A | 8/1995 | Oakes et al. | |
| 5,489,434 A | 2/1996 | Oakes et al. | |
| 5,494,588 A | 2/1996 | LaZonby | |
| 5,508,046 A | 4/1996 | Cosentino et al. | |
| 5,512,309 A | 4/1996 | Bender et al. | |
| 5,527,898 A | 6/1996 | Bauer et al. | |
| 5,578,134 A | 11/1996 | Lentsch et al. | |
| 5,591,706 A | 1/1997 | Ploumen | |
| 5,595,967 A | 1/1997 | Miracle et al. | |
| 5,597,790 A | 1/1997 | Thoen | |
| 5,616,335 A | 4/1997 | Nicolle et al. | |
| 5,616,616 A | 4/1997 | Hall et al. | |
| 5,632,676 A | 5/1997 | Kurschner et al. | |
| 5,641,530 A | 6/1997 | Chen | |
| 5,656,302 A | 8/1997 | Cosentino et al. | |
| 5,658,467 A | 8/1997 | LaZonby et al. | |
| 5,674,538 A | 10/1997 | Lokkesmoe et al. | |
| 5,674,828 A | 10/1997 | Knowlton et al. | |
| 5,683,724 A | 11/1997 | Hei et al. | |
| 5,712,239 A | 1/1998 | Knowlton et al. | |
| 5,718,910 A | 2/1998 | Oakes et al. | |
| 5,756,139 A | 5/1998 | Harvey et al. | |
| 5,785,867 A | 7/1998 | LaZonby et al. | |
| 5,840,343 A | 11/1998 | Hall et al. | |
| 5,851,483 A | 12/1998 | Nicolle et al. | |
| 5,891,392 A | 4/1999 | Monticello et al. | |
| 5,900,256 A | 5/1999 | Scoville, Jr. et al. | |
| 5,902,619 A | 5/1999 | Rubow et al. | |
| 5,962,392 A * | 10/1999 | Revell et al. | 510/372 |
| 5,968,539 A | 10/1999 | Beerse et al. | |
| 5,989,611 A | 11/1999 | Stemmler, Jr. et al. | |
| 6,010,729 A | 1/2000 | Gutzmann et al. | |
| 6,024,986 A | 2/2000 | Hei | |
| 6,033,705 A | 3/2000 | Isaacs | |
| 6,049,002 A | 4/2000 | Mattila et al. | |
| 6,080,712 A * | 6/2000 | Revell et al. | 510/372 |
| 6,096,226 A | 8/2000 | Fuchs et al. | |
| 6,096,266 A | 8/2000 | Duroselle | |
| 6,096,348 A | 8/2000 | Miner et al. | |
| 6,274,542 B1 * | 8/2001 | Carr et al. | 510/376 |

* cited by examiner

HIGH CONCENTRATION MONOESTER PEROXY DICARBOXYLIC ACID COMPOSITIONS, USE SOLUTIONS, AND METHODS EMPLOYING THEM

FIELD OF THE INVENTION

The present invention relates to high concentration compositions of a monoester peroxy dicarboxylic acid, use solutions, methods employing these compositions, and methods of making these compositions.

BACKGROUND OF THE INVENTION

Monoester peroxy dicarboxylic acid compositions exhibit useful antimicrobial activity. Synthesis of monoester peroxy dicarboxylic acids is known, as is their use as antimicrobial agents in cleaning products and methods. Existing compositions including monoester peroxy dicarboxylic acids suffer from unacceptable decomposition of the monoester peroxy dicarboxylic acid, or unacceptable stabilizing agents in the composition. Existing compositions also suffer from low concentrations of active monoester peroxy dicarboxylic acid.

SUMMARY OF THE INVENTION

The present invention relates to high concentration compositions of a monoester peroxy dicarboxylic acid, use solutions, methods employing these compositions, and methods of making these compositions.

In one embodiment, the high concentration composition of a monoester peroxy dicarboxylic acid includes at least about 6 wt-% monoester peroxy dicarboxylic acid, at least about 10 wt-% diester dicarboxylate, at least about 4 wt-% hydrogen peroxide, and less than about 55 wt-% total water. In another embodiment, the high concentration composition is a high concentration diester dicarboxylate-peroxide composition, which includes at least about 20 wt-% diester dicarboxylate, at least about 10 wt-% hydrogen peroxide, and less than about 40 wt-% total water. After it is formed, the high concentration diester dicarboxylate-peroxide composition will form an equilibrium mixture. This equilibrium mixture of monoester peroxy dicarboxylic acid, diester dicarboxylate, hydrogen peroxide, and water provides an embodiment of the high concentration composition of a monoester peroxy dicarboxylic acid.

In each of these embodiments, the high concentration composition can also include one or more surfactants and/or an inert organic solvents, antimicrobial solvents, acidulants, chelants, buffering agents, or stabilizing agents, or mixtures thereof. Especially useful surfactants include anionic-types such as sulfonates and carboxylates, or amine oxides. In one preferred embodiment, the high concentration composition of a monoester peroxy dicarboxylic acid includes at least about 6 wt-% monoester peroxy dicarboxylic acid, at least about 10 wt-% diester dicarboxylate, at least about 4 wt-% hydrogen peroxide, and less than about 55 wt-% total water, and a surfactant. Preferred surfactants include a sulfate derivative, a sulfonate derivative, a phosphate derivative, a phosphonate derivative, a carboxylate derivative, an amine oxide derivative, or a mixture thereof.

In an embodiment, the present invention includes an antimicrobial use solution that includes monoester peroxy dicarboxylic acid and a surfactant, preferably an anionic surfactant, an amine oxide surfactant, or a mixture there. The use solution typically also include a carrier or solvent, such as water, and other ingredients of the high concentration composition. A preferred antimicrobial use solution includes from about 5 ppm to about 500, preferably about 10 ppm to about 300 ppm, most preferably from about 20 ppm to about 200 ppm monoester peroxy dicarboxylic acid; from 2 ppm to about 1200 ppm, preferably from about 5 ppm to about 700 ppm, most preferably from about 10 ppm to about 400 ppm anionic surfactant; from about 2 ppm to about 1200 ppm, preferably from about 5 ppm to about 700 ppm, most preferably from about 10 ppm to about 400 ppm amine oxide surfactant; or a mixture thereof; with total surfactant being greater than about 10 ppm; and also including carrier.

In another embodiment, the invention includes a method employing a use solution of the high concentration composition of the invention to reduce a population of one or more microorganisms on an object, such as on a surface or in a fluid. In an embodiment, the invention includes a method employing a use solution of the high concentration composition of the invention to reduce the population of a microorganism on skin or to treat a disease of skin. In an embodiment, the invention includes a method employing a use solution of the high concentration composition of the invention to reduce an odor of an object, such as of a surface or of a fluid. In an embodiment, the invention includes a method employing a use solution of the high concentration composition of the invention to bleach an object. These methods include contacting the object with a use solution of a high concentration monoester peroxy dicarboxylic acid composition of the invention. Contacting can include spraying the composition, immersing the object in the composition, fogging, wiping, injecting, dripping, foam or gel treating the object with the composition, or a combination thereof.

DETAILED DESCRIPTION OF THE INVENTION

Definitions

As used herein, the term "alcohol" refers to a broad class of hydroxyl-containing organic compounds. Alcohols include monohydric, dihydric, trihydric, and polyhydric alcohols. Monohydric alcohols include aliphatic, alicyclic, aromatic, heterocyclic, or polycyclic alcohols. Aliphatic alcohols include paraffinic and olefinic alcohols. Dihydric alcohols, also known as diols, have two hydroxyl groups and include glycols and other derivatives. Trihydric alcohols have three hydroxyl groups and include glycerol and its derivatives. Polyhydric alcohols are also known as polyols.

As used herein, the term "$C_2$ or higher alcohol" refers to alcohols with more than 1 carbon atom, e.g., 2 or more carbon atoms. This term excludes methanol. $C_2$ or higher alcohols include monohydric, dihydric, trihydric, and polyhydric alcohols with more than 1 carbon atom. Alcohols with more than 1 carbon atom can also be referred to as hydroxy alkyl derivatives.

As used herein, the term "microorganisms" refers to any noncellular or unicellular (including colonial) organism. Microorganisms include all prokaryotes. Microorganisms include bacteria (including cyanobacteria and Mycobacteria), lichens, microfungi, protozoa, virinos, viroids, viruses, and some algae. As used herein, the term "microbe" is synonymous with microorganism.

As used herein, the term "object" refers to something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

As used herein, the phrase "food product" includes any food substance that might require treatment with an antimicrobial agent or composition and that is edible with or without further preparation. Food products include meat (e.g., red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, harvested or growing plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched or pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, cooling towers, pools or fountains, pasteurizers, dental lines, produce spray applications for grocers, meat chillers, storefront collers, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a high concentration composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, weight percent (wt-%), percent by weight, % by weight, and the like are synonyms that refer to the concentration of a substance as the weight of that substance divided by the weight of the composition and multiplied by 100.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3–1 $\log_{10}$. In this application, such a population reduction is the minimum acceptable for the processes. Any increased reduction in population of microorganisms is an added benefit that provides higher levels of protection.

High Concentration Equilibrium Derived Monoester Peroxy Dicarboxylic Acid Compositions The present invention relates to high concentration equilibrium compositions containing a monoester peroxy dicarboxylic acid. Typically, the high concentration compositions include concentrations of diester dicarboxylate, monoester peroxy dicarboxylic acid, and hydrogen peroxide that are larger than in conventional compositions. The high concentration compositions can also include a surfactant and/or an inert organic solvent at concentrations effective to enhance the concentration of diester dicarboxylate and/or monoester peroxy dicarboxylic acid in the composition. Typically, the monoester peroxy dicarboxylic acid is an antimicrobial agent.

Surprisingly, monoester peroxy dicarboxylic acid compositions can include a higher concentration of monoester peroxy dicarboxylic acid than had been achieved with conventional compositions. The high concentration compositions of the present invention typically include more than 6 wt-% monoester peroxy dicarboxylic acid, preferably at least about 7 wt-% monoester peroxy dicarboxylic acid, more preferably at least about 11 wt-% monoester peroxy dicarboxylic acid, most preferably at least about 13 wt-% monoester peroxy dicarboxylic acid, more preferably at least about 15 wt-% monoester peroxy dicarboxylic acid. The maximum amount of monoester peroxy dicarboxylic acid that can be achieved in the composition is typically about 35 wt-%, preferably about 24 wt-%, more preferably about 15 wt-%. These high concentrations of equilibrium monoester peroxy dicarboxylic acids can be achieved in compositions of the invention employing only diester dicarboxylate, hydrogen peroxide, optional stabilizers or acid catalysts, and any side products from reactions of these species. Such minimal compositions typically include less water and/or more hydrogen peroxide than conventional compositions.

High concentrations of monoester peroxy dicarboxylic acid can also be achieved in compositions of the invention employing one or more adjuvants, such as a surfactant and/or an inert organic solvent.

Preferred high concentration monoester peroxy dicarboxylic acid compositions include at least about 10 wt-% diester dicarboxylate, preferably at least about 15 wt-% diester dicarboxylate, and most preferably at least about 20 wt-%, or more. The maximum amount of diester dicarboxylate that can be achieved in the composition is typically about 75 wt-%, preferably about 55 wt-%, more preferably about 30 wt-%.

Preferred high concentration monoester peroxy dicarboxylic acid compositions include at least about 4 wt-% hydrogen peroxide, preferably at least about 6 wt-% hydrogen peroxide, more preferably at least about 8 wt-% hydrogen peroxide, or more. The maximum amount of hydrogen peroxide that can be achieved in the composition is typically about 45 wt-%, preferably about 25 wt-%, more preferably about 15 wt-%.

Preferred high concentration equilibrium monoester peroxy dicarboxylic acid compositions include less than about 55 wt-% total water, preferably less than about 45 wt-% total water, more preferably less than about 35 wt-% total water. Lower levels of water can be achieved by desiccating, evaporating, distilling, or reacting formed water in the equilibrium system. Monoester peroxy dicarboxylic acid, diester dicarboxylate, hydrogen peroxide, and water are involved in an equilibrium in the high concentration composition of the invention. The minimum amount of water that can be achieved in the high concentration compositions typically is about 50 wt-%, preferably about 20 wt-%, more preferably about 15 wt-%, most preferably about 8 wt-%.

The compositions and methods of the present invention include compositions that, upon reaching equilibrium, yield the high concentration monoester peroxy dicarboxylic acids of the present invention. The high concentration monoester peroxy dicarboxylic acid of the present invention can be formulated as a high concentration diester dicarboxylate-peroxide composition. The high concentration diester dicarboxylate-peroxide composition typically includes diester dicarboxylate, hydrogen peroxide, water, optionally, stabilizer, and any products from reactions of these species. Such minimal compositions typically include less water and/or more hydrogen peroxide and diester dicarboxylate than conventional compositions.

The high concentration diester dicarboxylate-peroxide composition can also include one or more adjuvants, such as an acidulant, a buffering agent, a chelant, surfactant, and/or an inert organic solvent. The additional ingredients (e.g. surfactant, inert organic solvent, stabilizer, alcohol, and the like), and their amounts, described for the monoester peroxy dicarboxylic acid compositions are also suitable for the high concentration diester dicarboxylate-peroxide compositions.

Sanitizing Compositions

The present invention also includes use or sanitizing compositions including a monoester peroxy dicarboxylic acid and a surfactant, preferably an anionic surfactant and/or an amine oxide surfactant. These use or sanitizing compositions can be made from the present high concentration compositions. Such sanitizing or use solutions can be suitable for any of several sanitizing applications. For example, the present high concentration compositions can be used to produce non-food contact antimicrobial compositions, disinfectant compositions, food contact sanitizers, antimicrobial compositions with increased rate of kill, antimicrobial compositions effective at elevated temperatures, such as 120° C., compositions that reduce the population of microorganisms that cause tuberculosis, and the like. In general, one of skill in the art will know that applications that require a greater reduction in the population of a microorganism or that involve a more challenging environment will require a stronger antimicrobial composition. Such a stronger antimicrobial composition can include a larger proportion of the high concentration compositions, or a high concentration composition having a higher concentration of one or more of the ingredients, such as the monoester peroxy dicarboxylic acid, the surfactant, or the cosolvent.

Suitable use or sanitizing solutions can include concentrations of surfactant, preferably anionic and/or amine oxide surfactant, and monoester peroxy dicarboxylic acid effective for reducing the concentration of one or more microorganisms and/or achieving sanitizing. For example, such use or sanitizing solutions can include about 2 ppm up to 1500 ppm anionic surfactant, preferably from about 5 to about 700 ppm of anionic surfactant, more preferably from about 10 to about 400 ppm of anionic surfactant; most preferably from about 20 to about 250 ppm of anionic surfactant. For example, such use or sanitizing solutions can include from about 2 to about 1500 ppm of amine oxide surfactant, more preferably from about 5 to about 700 ppm of amine oxide surfactant; most preferably from about 10 to about 250 ppm of amine oxide surfactant. Typically the surfactant is present at levels greater than about 10 ppm. For example, such use or sanitizing solutions can include from about 5 to about 500 ppm of monoester peroxy dicarboxylic acid, more preferably from about 10 to about 300 ppm of monoester peroxy dicarboxylic acid; most preferably from about 20 to about 200 ppm of monoester peroxy dicarboxylic acid.

Suitable non-food contact antimicrobial use solutions typically include concentrations of surfactant, preferably anionic surfactant and/or amine oxide surfactant, and monoester peroxy dicarboxylic acid effective for reducing the concentration of one or more microorganisms on an object that is not food. For example, such non-food contact antimicrobial use solutions can include from about 2 to about 800 ppm of anionic surfactant, preferably from about 5 to about 400 ppm of anionic surfactant; more preferably from about 10 ppm to about 250 ppm of anionic surfactant. For example, such use solutions can include from about 2 to about 1500 ppm of amine oxide surfactant, more preferably from about 5 to about 700 ppm of amine oxide surfactant, most preferable from about 10 to about 250 ppm. For example, such non-food contact antimicrobial use solutions can include from about 5 to about 700 ppm of monoester peroxy dicarboxylic acid, preferably from about 5 to about 400 ppm of monoester peroxy dicarboxylic acid; more preferably from about 5 to about 200 ppm of monoester peroxy dicarboxylic acid.

Suitable food contact sanitizers typically include concentrations of surfactant, preferably anionic surfactant, and monoester peroxy dicarboxylic acid effective for sanitizing food. For example, such use solutions can include from about 2 to about 1200 ppm of anionic surfactant, preferably from about 2 to about 600 ppm of anionic surfactant, more preferably from about 2 to about 200 ppm of anionic surfactant. For example, such use solutions can include from about 5 to about 700 ppm of monoester peroxy dicarboxylic acid, more preferably from about 5 to about 400 ppm of monoester peroxy dicarboxylic acid; most preferably from about 5 to about 200 ppm of monoester peroxy dicarboxylic acid.

Suitable antimicrobial use solutions with increased rate of kill typically include concentrations of surfactant, preferably anionic surfactant and/or amine oxide surfactant, and monoester peroxy dicarboxylic acid effective increased rate of kill. For example, such use solutions can include from about 2 to about 1500 ppm of anionic surfactant, preferably from about 5 to about 700 ppm of anionic surfactant, more preferably from about 10 to about 240 ppm of anionic surfactant. For example, such compositions can include from about 2 to about 1500 ppm of amine oxide surfactant, preferably from about 5 to about 700 ppm of amine oxide surfactant, more preferably from about 10 to about 240 ppm of amine oxide surfactant. For example, such compositions can include from about 5 to about 1500 ppm of monoester peroxy dicarboxylic acid, more preferably from about 5 to about 600 ppm of monoester peroxy dicarboxylic acid; most preferably from about 5 to about 200 ppm of monoester peroxy dicarboxylic acid.

Suitable antimicrobial use solutions effective at elevated temperatures, such as 120 ° C., typically include concentrations of surfactant, preferably anionic surfactant and/or amine oxide surfactant, and monoester peroxy dicarboxylic acid effective antimicrobial action at elevated temperatures. For example, such use solutions can include from about 2 to about 15000 ppm of anionic surfactant, preferably from about 5 to about 7000 ppm of anionic surfactant, more preferably from 10 to about 1000 ppm of anionic surfactant. For example, such use solutions can include from about 2 to about 15000 ppm of amine oxide surfactant, preferably from about 5 to about 7000 ppm of amine oxide surfactant, more preferably from about 10 to about 1000 ppm of amine oxide surfactant. For example, such use solutions can include from about 5 to about 7000 ppm of monoester peroxy dicarboxylic acid, more preferably from about 5 to about 4000 ppm of monoester peroxy dicarboxylic acid; most preferably from about 10 to about 2000 ppm of monoester peroxy dicarboxylic acid.

Suitable antimicrobial use solutions with activity against microorganisms that cause tuberculosis typically include concentrations of surfactant, preferably anionic surfactant and/or amine oxide surfactant, and monoester peroxy dicarboxylic acid effective to reduce the population of one or more organisms that cause tuberculosis. For example, such use solutions can include from about 2 to about 15,000 ppm of anionic surfactant, preferably from about 5 to about 7,000 ppm of anionic surfactant, more preferably from about 50 to about 1000 ppm of anionic surfactant. For example, such use solutions can include from about 5 to about 500 ppm of fatty acid, such as octanoic acid, preferably from about 10 to about 250 ppm of such a fatty acid, more preferably from 20 to about 100 ppm of such a fatty acid. For example, such use solutions can include from about 5 to about 7,000 ppm of monoester peroxy dicarboxylic acid, more preferably from about 50 to about 4000 ppm of monoester peroxy dicarboxylic acid; most preferably from about 130 to about 1000 ppm of monoester peroxy dicarboxylic acid.

Surfactant

Preferred high concentration monoester peroxy dicarboxylic acid compositions include at least about 1 wt-% surfactant, preferably at least about 2 wt-% surfactant, and most preferably at least about 2.5 wt-% surfactant. Typically the maximum amount of surfactant in a high concentration composition according to the invention is about 1–25 wt-%, preferably about 1–15 wt-%, more preferably about 1–10 wt-%, most preferably about 1–5 wt-% Suitable surfactants include nonionic surfactants, anionic surfactants, cationic surfactants, amphoteric surfactants, amine oxides, and the like. Preferred surfactants include anionic surfactants and amine oxides. Suitable surfactants which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), arnine oxides (mono-, di-, or tri-alkyl) and $C_8$–$C_{10}$ alkyl glucosides.

Surfactants suitable for use in the present compositions and methods include n-octanesulfonate, available as NAS 8D from Ecolab, n-octyl dimethylamine oxide, n-decyl dimethyl amine oxide, cocoa dimethylamine oxide, and the commonly available aromatic sulfonates such as the alkyl benzene sulfonates (e.g. dodecylbenzene sulfonate, cumene sulfonate, xylene sulfonates) or naphthalene sulfonates. Most preferred anionic surfactants include C6–C24 alkylbenzene sulfonates, C6–C24 olefin sulfonates, C6–C24 paraffin sulfonates, cumene sulfonate, xylene sulfonate, C6–C24 alkyl naphthalene sulfonates, C6–C24 alkyl or dialkyl diphenyl ether sulfonates or disulfonates, C4–C24 mono or dialkyl sulfosuccinates, sulfonated or sulfated fatty acids, C6–C24 alcohol sulfates (preferably C6–C12 alcohol sulfates), C6–C24 alcohol ether sulfates having 1 to about 20 ethylene oxide groups, and C4–C24 alkyl, aryl or alkaryl phosphate esters or their alkoxylated analogs having 1 to about 40 ethylene, propylene or butylene oxide units, or mixtures thereof. Additional suitable surfactants include nonionic surfactants of C6–C24 alcohol ethoxylates (preferably C6–C14 alcohol ethoxylates) having 1 to about 20 ethylene oxide groups (preferably about 9 to about 20 ethylene oxide groups); C6–C24 alkylphenol ethoxylates (preferably C8–C10 alkylphenol ethoxylates) having 1 to about 100 ethylene oxide groups (preferably about 12 to about 20 ethylene oxide groups); C6–C24 alkylpolyglycosides (preferably C6–C20 alkylpolyglycosides) having 1 to about 20 glycoside groups (preferably about 9 to about 20 glycoside groups); C6–C24 fatty acid ester ethoxylates, propoxylates or glycerides; and C4–C24 mono or dialkanolamides.

A particularly useful nonionic surfactant for use as a defoamer is nonylphenol having an average of 12 moles of ethylene oxide condensed thereon, it being end capped with a hydrophobic portion including an average of 30 moles of propylene oxide.

Highly preferred surfactants include food grade surfactants, such as linear alkylbenzene sulfonic acids and their salts, and ethylene oxide/propylene oxide derivatives sold under the Pluronic™ trade name. A most preferred surfactant is compatible as an indirect or direct food additive or substance; especially those described in the Code of Federal Regulations (CFR), Title 21—Food and Drugs, parts 170 to 186 (which is incorporated herein by reference).

Preferably the surfactant is present at about 0.1 to about 25 wt-% of the composition, more preferably about 0.1 to about 20 wt-%, and most preferably about 0.1 to about 10 wt-%.

Solvent or Co-solvent

Preferred high concentration monoester peroxy dicarboxylic acid compositions include an inert organic co-solvent such as amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Mixtures of cosolvents can be used if desired.

Ethylene glycol butyl ether and dipropylene glycol n-butyl ether are particularly preferred cosolvents.

Commercially available cosolvents (all of which are available from Union Carbide Corp.) include Butoxyethyl PROPASOL™, Butyl CARBITOL™. acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

A most preferred co-solvent is be compatible as an indirect or direct food additive or substance; especially those described in the Code of Federal Regulations (CFR), Title 21—Food and Drugs, parts 170 to 186 (which is incorporated herein by reference).

Inert organic co-solvents are preferably present at a concentration of about 0 to about 30 wt-%, preferably about 0 to about 15 wt-%, most preferably about 0 to about 5 wt-%.

Preferred high concentration monoester peroxy dicarboxylic acid compositions can also include an organic solvent such as amyl acetate, amyl alcohol, a $C_1$ or greater alkyl alcohols. Such alcohols may be linear or branched and contain mixtures of the alcohols. The alcohols may be monohydric, dihydric or polyhydric as described previously.

Certain solvents can be useful as antimicrobial synergistic agents in the compositions. Such antimicrobially active solvents include acetamidophenol, acetanilide, acetophenone, 2-acetyl-1-methylpyrrole, benzyl acetate, benzyl alcohol, benzyl benzoate, benzyloxyethanol, ethers or hydroxyethers such as ethylene glycol phenyl ether, and propylene glycol phenyl ether; essential oils (e.g., benzaldehyde, pinenes, terpineols, terpinenes, carvone, cinnamealdehyde, borneol and its esters, citrals, ionenes, jasmine oil, limonene, dipentene, linalool and its esters); dialkyl carbonates such as dimethyl carbonate, diethyl carbonate, dipropyl carbonate, diisopropyl carbonate, and dibutyl carbonate; $C_{1-12}$ organic anhydrides such as acetic anhydride, succinic anhydride, phthalic anhydride, maleic anhydride, and alkyl or alkenyl succinic anhydrides; organonitriles such as benzonitrile; organo-phosphates and phosphonates such as tributyl phosphate, tripropyl phosphate, 2-ethyl-1-hexyl phosphate; and phthalate esters such as dibutyl phthalate, diethylhexyl phthalate, and diethyl phthalate. Benzyl alcohol, phenylethanol, essential oils, dibasic esters, dialkyl carbonates, ethylene glycol phenyl ether and propylene glycol phenyl ether are particularly preferred antimicrobially-active solvents. Mixtures of antimicrobially-active solvents can be used if desired.

Inert or antimicrobially active organic solvents are preferably present at a concentration of about 0 to about 30 wt-%, preferably about 0 to about 15 wt-%, most preferably about 0 to about 5 wt-%.

Monoester Peroxy Dicarboxylic Acids

As used herein, monoester peroxy dicarboxylic acid refers to a molecule having the formula:

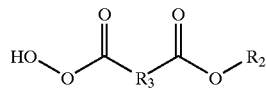

In this formula, $R_2$ and $R_3$ can independently be any of a wide variety of organic groups (e.g. alkyl, linear or cyclic, aromatic or saturated) or substituted organic groups (e.g., with one or more heteroatoms or organic groups). Monoester peroxy dicarboxylic acid can be made using methods typically employed for producing peroxycarboxylic acid, such as incubating the corresponding diester dicarboxylate with hydrogen peroxide.

Preferred monoester peroxy dicarboxylic acids include all monoester peroxy dicarboxylic acids, preferably having the formula:

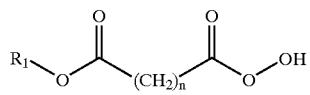

where $R_1$ represents an alkyl group having from 1 to 8 carbons and n is 0 to 6, preferably 1 to 5. The alkyl group can be either straight chain or branched. Preferably, $R_1$ is a methyl, ethyl, propyl (n-, iso-), butyl (n-, iso-, tert-), n-amyl, n-hexyl, or 2-ethylhexyl group. Preferably, n is 2, 3, 4, or 5. In one preferred embodiment, the composition of the present invention includes a mixture of alkyl ester peroxycarboxylic acids in which n is 2, 3, and 4. Such a mixture includes monoesters of peroxyadipic, peroxyglutaric, and peroxysuccinic acids. In another preferred embodiment, a majority of the ester peroxycarboxylic acid in the composition has x equal to 3. In a preferred embodiment, $R_1$ is a $C_1$–$C_8$ alkyl. In a preferred embodiment, n is 1, 2, 3, or 4. Most preferably, $R_1$ is a $C_1$ alkyl, $C_2$ alkyl, $C_3$ alkyl, or $C_4$ alkyl, and n is 2, 3 or 4, or a combination thereof. In another most preferred embodiment, $R_1$ is a $C_5$–$C_8$ alkyl, n is 5 or 6.

Alkyl ester peroxycarboxylic acids useful in this invention include monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxysebacic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid, monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxysebacic acid, in which propyl can be n- or iso-propyl; monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxysebacic acid, in which butyl can be n-, iso-, or t-butyl; monoamyl monoperoxyoxalic acid, monoamyl monoperoxymalonic acid, monoamyl monoperoxysuccinic acid, monoamyl monoperoxyglutaric acid, monoamyl monoperoxyadipic acid, monoamyl monoperoxysebacic acid, in which amyl is n-; monohexyl monoperoxysebacic acid, in which hexyl is n-; mono-2-ethylhexyl monoperoxysebacic acid.

High concentration compositions of monoester peroxy dicarboxylic acid can also include other ingredients, for example, to maintain the pH of the composition or the stability of the monoester peroxy dicarboxylic acid. Preferably the high concentration composition includes a buffer. Preferred buffers maintain the pH of the composition, after dilution to the use concentration, below about 7, preferably below about 5, and more preferably below about 4. Preferred buffers include citric acid and its salts, phosphoric acid and its salts, succinic acid and its salts, adipic acid and its salts, glutaric acid and its salts, acetic acid and its salts, boric acid and its salts, and mixtures thereof. Preferably the buffer is present at about 0 to about 20 wt-% of the composition, preferably about 0 to about 10 wt-%, and most preferably about 0 to about 7 wt-%.

Preferably the high concentration composition includes an alcohol. Preferred alcohols stabilize the monoester peroxy dicarboxylic acid at non-toxic concentrations of the alcohol. Preferred alcohols include a $C_2$ or higher alcohol effective for stabilizing the monoester peroxy dicarboxylic acid at non-toxic concentration of the alcohol. The $C_2$ or higher alcohol can include a mono-, di-, or tri-hydric alcohol, such as a straight chain or branched aliphatic or C2–C12 hydroxy derivative, for example, ethanol, n-propanol, iso-propanol, n-butanol, sec-butanol, iso-butanol, n-pentanol, propylene glycol, butylene glycol, hexylene glycol, glycerine, polyethylene glycol, polypropylene glycol, polybutylene glycol, and the like, or a combination thereof. The $C_2$ or higher alcohol can be present at effective concentrations in the range of about 1 wt-% to about 80 wt-%.

Preferably, the high concentration monoester peroxy dicarboxylic acid composition maintains suitable levels of the monoester peroxy dicarboxylic acid, or a stable transesterified derivative, in the composition. Preferably, the amount or concentration of monoester peroxy dicarboxylic acid remains at more than about 50 wt-% for at least about 3 months, preferably at more than about 70 wt-%, and most preferably at more than about 85 wt-%.

Preferably, the high concentration monoester peroxy dicarboxylic acid retains antimicrobial activity. Preferably, upon formulating according to the invention, the monoester peroxy dicarboxylic acid composition retains at least about 30% of its antimicrobial activity for at least about 3 months, preferably at more than about 50%, and most preferably at more than about 70%.

The high concentration compositions of the invention can be formulated as a liquid, a gel, an aerosol, a gas, a wax, a solid, or a powder, or as a solution or suspension containing such a composition.

Diester Dicarboxylates

As used herein, diester dicarboxylate refers to a molecule having the formula:

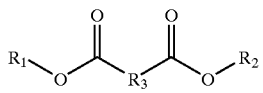

In this formula, $R_1$, $R_2$, and $R_3$ can independently be any of a wide variety of organic groups (e.g. alkyl, linear or cyclic, aromatic or saturated) or substituted organic groups (e.g., with one or more heteroatoms or organic groups). Diester dicarboxylate can be converted to monoester peroxy dicarboxylic acid, for example, by incubating the corresponding diester dicarboxylate with hydrogen peroxide.

Preferred diester dicarboxylates include alkyl diester dicarboxylates, preferably having the formula:

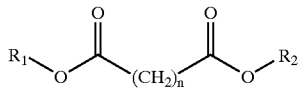

where $R_1$ and $R_2$ represent independently an alkyl group having from 1 to 8 carbons, preferably 1 to 5, and n is 0 to 6, preferably 1 to 5. The alkyl group can be either straight chain or branched. Preferably, $R_1$ and R2 are independently a methyl, ethyl, propyl (n-, iso-), butyl (n-, iso-, tert-), n-amyl, n-hexyl, or 2-ethylhexyl group. Preferably, n is 2, 3, 4, or 5. In one preferred embodiment, the composition of the present invention includes a mixture of alkyl diester dicarboxylates in which x is 2, 3, and 4. Such a mixture includes diesters of peroxyadipic, peroxyglutaric, and peroxysuccinic acids. In another preferred embodiment, a majority of the alkyl diester dicarboxylates in the composition has n equal to 3 or 4. In yet another preferred embodiment, a majority of the alkyl diester dicarboxylates in the composition has n equal to 5. In a preferred embodiment, $R_1$ and $R_2$ are independently a $C_1$–$C_8$ alkyl. In a preferred embodiment, n is 1, 2, 3, or 4. Most preferably, $R_1$ and $R_2$ are independently a $C_1$ alkyl, $C_3$ alkyl, $C_4$ alkyl, and n is 2, 3 4, or 5. In another preferred embodiment, $R_1$ and $R_2$ are independently a $C_5$–$C_8$ alkyl, n is 5 or 6.

Alkyl diester dicarboxylates useful in this invention include all symmetrical and mixed diesters of oxalic acid, malonic acid, succinic acid, glutaric acid, adipic acid, or sebacic acid (or mixtures thereof) with methanol, ethanol, propanol (e.g., n-propanol or isopropanol), butanol (e.g., n-butanol, iso-butanol, or tert-butanol), amyl alcohol (n-pentanol, iso-pentanol, sec-pentanol, or tert-pentanol), hexanol (n-hexanol, iso-hexanol, sec-hexanol, or tert-hexanol), octanol (n-octanol, iso-octanol, sec-octanol, or tert-octanol) or mixtures thereof. Such alkyl diester dicarboxylates include dimethyl oxalate, methyl ethyl oxalate, methyl propyl oxalate, methyl butyl oxalate, dimethyl malonate, methyl ethyl malonate, methyl propyl malonate, methyl butyl malonate, dimethyl succinate, methyl ethyl succinate, methyl propyl succinate, methyl butyl succinate, dimethyl glutarate, methyl ethyl glutarate, methyl propyl glutarate, methyl butyl glutarate, dimethyl adipate, methyl ethyl adipate, methyl propyl adipate, methyl butyl adipate, dimethyl sebacate, methyl ethyl sebacate, methyl propyl sebacate, methyl butyl sebacate, diethyl oxalate, ethyl propyl oxalate, ethyl butyl oxalate, diethyl malonate, ethyl propyl malonate, ethyl butyl malonate, diethyl succinate, ethyl propyl succinate, ethyl butyl succinate, diethyl glutarate, ethyl propyl glutarate, ethyl butyl glutarate, diethyl adipate, ethyl propyl adipate, ethyl butyl adipate, diethyl sebacate, ethyl propyl sebacate, ethyl butyl sebacate, dipropyl oxalate, propyl butyl oxalate, dipropyl malonate, propyl butyl malonate, dipropyl succinate, propyl butyl succinate, dipropyl glutarate, propyl butyl glutarate, dipropyl adipate, propyl butyl adipate, dipropyl sebacate, propyl butyl sebacate, dibutyl oxalate, dibutyl malonate, dibutyl succinate, dibutyl glutarate, dibutyl adipate, dibutyl sebacate, diamyl succinate, diamyl glutarate, diamyl adipate, diamyl sebacate, dihexyl succinate, dihexyl glutarate, dihexyl adipate, dihexyl sebacate, diethylhexyl succinate, diethylhexyl glutarate, diethylhexyl adipate, diethylhexyl sebacate, or mixtures thereof. In these esters propyl can be n- or iso-propyl; butyl can be n-, iso-, or tert-butyl; amyl can be n-, sec-, iso-, tert-amyl; hexyl can be n-, sec-, iso-, tert-hexyl; and octyl can be n-, iso-, sec-, tert-octyl, or 2-ethylhexyl-, or a mixture thereof.

The methods and compositions of the present invention can also include diester dicarboxylates known as dibasic esters and available under the trade designations DBE, DBE-3, DBE-4, DBE-5, DBE-6, DBE-9, DBE-IB, and DBE-ME from DuPont Nylon. These "DBEs" include single isolates or mixtures of species such as dimethyl adipate, dimethyl succinate, dimethyl glutarate, and diisobutyl adipate, diisobutyl succinate, and diisobutyl glutarate. Other diester dicarboxylates, such as dioctyl sebacate, bis-[2-ethylhexyl] sebacate, diamyl sebacate, are also commercially available in relatively pure form. These DBEs and the sebacate esters are preferred, in part, since they are commercially and economically available. Additional suitable diester dicarboxylates (or dibasic esters) include dimethyl malonate, dimethyl sebacate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate.

Peroxycarboxylic Acid Antimicrobial Compositions
Compositions of Carboxylic Acids and Peroxycarboxylic Acids Among other constituents, the composition of the present invention includes a carboxylic acid. Generally, carboxylic acids have the formula R-COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Carboxylic acids can have one, two, three, or more carboxyl groups. Preferred ester groups include aliphatic ester groups, such as $R_1OC(O)R_2$— where each of $R_1$ and $R_2$ can be aliphatic, preferably alkyl, groups described above for R. Preferably $R_1$ and $R_2$ are each independently small alkyl groups, such as alkyl groups with 1 to 4 carbon atoms.

The composition and methods of the invention can employ carboxylic acids containing as many as 18 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic (glycolic), neopentanoic, neoheptanoic, neodecanoic, oxalic, malonic, succinic, glutaric, adipic, pimelic and subric acid. Examples of suitable alkyl ester carboxylic acids include monomethyl oxalic acid, monomethyl malonic acid, monomethyl succinic acid, monomethyl glutaric acid, monomethyl adipic acid; monoethyl oxalic acid, monoethyl malonic acid, monoethyl succinic acid, monoethyl glutaric acid, monoethyl adipic acid; monopropyl oxalic acid, monopropyl malonic acid, monopropyl succinic acid, monopropyl glutaric acid, monopropyl adipic acid, in which propyl can be n- or isopropyl; monobutyl oxalic acid, monobutyl malonic acid, monobutyl succinic acid, monobutyl glutaric acid, monobutyl adipic acid, in which butyl can be n-, iso-, or t-butyl.

Carboxylic acids which are generally useful are those having one or two carboxyl groups where the R group is a primary alkyl chain having a length of $C_2$ to $C_{12}$. The primary alkyl chain is that carbon chain of the molecule having the greatest length of carbon atoms and directly appending carboxyl functional groups. Longer chain carboxylic acid analogues, including hexanoic, heptanoic, octanoic, nonanoic, and decanoic, can reduce surface tension to assist in wetting of hydrophobic surfaces like skin.

In a preferred embodiment, the antimicrobial composition includes one or more mono- or di-carboxylic acids having up to 18 carbon atoms. Preferred mono- or di-carboxylic acids having up to 18 carbon atoms include acetic acid, lactic acid, glycolic acid, citric acid, heptanoic acid, octanoic acid, nonanoic acid, or a mixture thereof. In another preferred embodiment, the antimicrobial composition includes an alpha-hydroxy mono- or di-carboxylic acid having from 3 to 6 carbon atoms, preferably lactic acid.

Carboxylic acids that are generally useful include ester carboxylic acids, such as alkyl ester carboxylic acids. Preferred alkyl ester carboxylic acids include those with the formula:

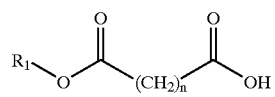

where $R_1$ represents an alkyl group having from 1 to 8 carbons and n is 0 to 6, preferably 1 to 5. The alkyl group can be either straight chain or branched. Preferably, $R_1$ is a methyl, ethyl, propyl (n-, iso-), butyl (n-, iso-tert-), n-amyl, n-hexyl, or 2-ethylhexyl group. Preferably, n is 2, 3, or 4. In one preferred embodiment, the composition of the present invention includes a mixture of alkyl ester peroxycarboxylic acids in which n is 2, 3, and 4. Such a mixture includes monoesters of peroxyadipic, peroxyglutaric, and peroxysuccinic acids. In another preferred embodiment, a majority of the ester peroxycarboxylic acid in the composition has n equal to 3. In a preferred embodiment, $R_1$ is a $C_1$–$C_4$ alkyl. In a preferred embodiment, n is 1, 2, 3, or 4. Most preferably, $R_1$ is a $C_1$ alkyl, $C_3$ alkyl, or $C_4$ alkyl, and n is 2, 3 or 4. In another preferred embodiment, $R_1$ is a $C_5$–$C_8$ alkyl, n is 5 or 6.

Suitable mono- or diester carboxylates for use in these in situ compositions include any of those described herein below. Preferred mono-dicarboxylates for in situ compositions of the present invention include the mono-ester dicarboxylic acids such as monomethyl oxalic acid, monomethyl malonic acid, monomethyl succinic acid, monomethyl glutaric acid, monomethyl adipic acid, monomethyl sebacic acid; monoethyl oxalic acid, monoethyl malonic acid, monoethyl succinic acid, monoethyl glutaric acid, monoethyl adipic acid, monoethyl sebacic acid; monopropyl oxalic acid, monopropyl malonic acid, monopropyl succinic acid, monopropyl glutaric acid, monopropyl adipic acid, monopropyl sebacic acid (n-, iso-), monobutyl oxalic acid, monobutyl malonic acid, monobutyl succinic acid, monobutyl glutaric acid, monobutyl adipic acid, monobutyl sebacic acid (n-, iso-, or tert-), monoamyl oxalic acid, monoamyl malonic acid, monoamyl succinic acid, monoamyl glutaric acid, monoamyl adipic acid, monoamyl sebacic acid (n-, iso-, sec-, or tert-), monohexyl oxalic acid, monohexyl malonic acid, monohexyl succinic acid, monohexyl glutaric acid, monohexyl adipic acid, monohexyl sebacic acid (n-, iso-, sec-, or tert-) monooctyl oxalic acid, monooctyl malonic acid, monooctyl succinic acid, monooctyl glutaric acid, monooctyl adipic acid, monooctyl sebacic acid (n-, iso-, sec-, 2-ethylhexyl-, or tert-).

Generally, the concentration of carboxylic acid within the composition used in the process of the invention ranges from about 0.5 wt-% to about 80 wt-%, preferably from about 5 wt-% to about 50 wt-%, and most preferably from about 10 wt-% to about 30 wt-%. Typically the concentration of ester carboxylic acid ranges up to about 15% by weight, although concentrations of up to 50% can be employed in certain embodiments, preferably from about 0.05 to about 15%, and most preferably from about 1% to about 9%.

Peroxycarboxylic (or percarboxylic) acids generally have the formula $R(CO_3H)_n$, where R is an alkyl, arylalkyl, cycloalkyl, aromatic, heterocyclic, or ester group, such as an alkyl ester group; and n is one, two, or three, and named by prefixing the parent acid with peroxy. Ester groups are defined as R groups including organic moieties (such as those listed above for R) and ester moieties. Preferred ester groups include aliphatic ester groups, such as $R_1OC(O)R_2$- where each of $R_1$ and $R_2$ can be aliphatic, preferably alkyl, groups described above for R. Preferably $R_1$ and $R_2$ are each independently small alkyl groups, such as alkyl groups with 1 to 5 carbon atoms.

While peroxycarboxylic acids are not as stable as carboxylic acids, their stability generally increases with increasing molecular weight. Thermal decomposition of these acids can generally proceed by free radical and non-radical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxyadipic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic and peroxysubric acid and mixtures thereof. Useful peroxycarboxylic acids also include the monoester peroxy dicarboxylic acids described herein above and compositions of the present invention including those monoester peroxy dicarboxylic acids.

Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids.

In a preferred embodiment, the composition of the invention utilizes a combination of several different peroxycarboxylic acids. Preferably, the composition includes one or more small $C_2$–$C_4$ peroxycarboxylic acids, one or more large $C_8$–$C_{12}$ peroxycarboxylic acids, and/or one or more alkyl monoester peroxy dicarboxylic acid compositions. Especially preferred is an embodiment in which the small peroxycarboxylic acid is peroxyacetic acid and the large acid is either peroxyoctanoic acid or peroxydecanoic acid.

In a preferred embodiment, the antimicrobial composition includes one or more alkyl monoester peroxy dicarboxylic acids and a peroxycarboxylic acid having from 2 to 12 carbon atoms. Preferably, such an antimicrobial composition includes peroxyacetic acid, or peroxyoctanoic acid, or peroxydecanoic acid, and monomethyl monoperoxyoxalic acid, monomethyl monoperoxymalonic acid, monomethyl monoperoxysuccinic acid, monomethyl monoperoxyglutaric acid, monomethyl monoperoxyadipic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, in which propyl can be n- or isopropyl; monobutyl monoperoxyoxalic acid, monobutyl monoperoxymalonic acid, monobutyl monoperoxysuccinic acid, monobutyl monoperoxyglutaric acid, monobutyl monoperoxyadipic acid, in which butyl can be n-, iso-, or t-butyl, or mixtures thereof. Preferably, in such mixtures the alkyl monoester peroxy dicarboxylic acids is one of the above, and the peroxycarboxylic acid having from 2 to 12 carbon atoms is peroxyacetic acid or peroxyoctanoic acid; combined in a ratio of about 1 to about 10 parts by weight of peroxyacetic acid per each 1 part of carboxylic acid. In another embodiment, when a blended acid is used, the peroxycarboxylic acids are blended in proportions that range from about 1 part to about 20 parts by weight of alkyl ester peroxyacid to mono- or di-peroxycarboxylic acid having up to 12 carbon atoms. In another preferred embodiment, the combination of peroxycarboxylic acid includes an alkyl ester peroxyacid and a mono- or di-peroxycarboxylic acid having up to 12 carbon atoms.

The amount of alkyl monoester peroxy dicarboxylic acid in use and concentrate compositions can range up to the limits at which the peroxycarboxylic acid can be dissolved or suspended in the composition. Preferably, the alkyl monoester peroxy dicarboxylic acid is present in a use or concentrate composition at a concentration of from about 0.0001 to about 20% by weight, preferably from about 0.05 to about 15% by weight, and more preferably from about 4 to about 10% by weight. Typically compositions include at least 0. 1%, preferably at least 1%, by weight alkyl monoester peroxy dicarboxylic acid.

A preferred antimicrobial high concentration monoester peroxy dicarboxylic acid composition of the present invention is effective for killing one or more of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold and the like. The compositions and methods of the present invention have activity against a wide variety of microorganisms such as Gram positive (for example, *Listeria monocytogenes*) and Gram negative (for example, *Escherichia coli*) bacteria, yeast, molds, bacterial spores, viruses, etc. The compositions and methods of the present invention, as described above, have activity against a wide variety of human pathogens. The compositions and methods can kill a wide variety of microorganisms on a food processing surface, on the surface of a food product, or in water used for washing or processing of food product.

A preferred antimicrobial high concentration monoester peroxy dicarboxylic acid composition of the present invention is effective for killing one or more of the pathogenic bacteria associated with a health care surfaces and environments, such as *Salmonella typhimurium, Staphylococcus aureus, Salmonella choleraesurus, Pseudomonas aeruginosa*, and *Escherichia coli*, mycobacteria, yeast, mold, and the like. The compositions and methods of the present invention have activity against a wide variety of microorganisms such as Gram positive (for example, *Staphylococcus aureus*) and Gram negative (for example, *Pseudomonas aeruginosa*) bacteria, yeast, molds, bacterial spores, viruses, etc. The compositions and methods of the present invention, as described above, have activity against a wide variety of human pathogens. The compositions and methods can kill a wide variety of microorganisms on a health care surface or in a health care environment.

The preferred compositions include concentrate compositions and use solutions. Typically, an antimicrobial concentrate composition can be diluted, for example with water, to form an antimicrobial use solution. In a preferred embodiment, the concentrate composition is diluted into water employed for washing or processing food product.

The advantageous stability of mixed peroxycarboxylic acid compositions in such methods, which include the presence of food product or health care debris or residue, makes these compositions competitive with cheaper, less stable, and potentially toxic chlorinated compounds. Preferred methods of the present invention include agitation or sonication of the use solution particularly as a concentrate is added to water to make the use solution. Preferred methods include water systems that have some agitation, spraying, or other mixing of the solution.

The level of reactive species, such as peroxy acids and/or hydrogen peroxide, in a use solution can be affected, typically diminished, by organic matter that is found in or added to the use solution. For example, when the use solution is a bath or spray used for washing food product, food product organic matter or accompanying organic matter will consume peroxy acid and peroxide. Thus, the amounts of ingredients listed for the use solutions refer to the composition before or early in use, with the understanding that the amounts will diminish as organic matter is added to the use solution.

In addition, the concentrate and changes with age. It is believed that in approximately one year at ambient conditions the amount of peroxycarboxylic acid in the compositions can decrease to about 50% to about 80%, preferably about 80% to about 85%, of the initial equilibrium values or concentrate levels. Such aged compositions are included in the scope of the present invention.

In an embodiment, the compositions of the present invention preferably include only ingredients that can be employed in food products or in food product washing, handling, or processing, for example, according to government (e.g., FDA or USDA) rules and regulations. Preferably, the composition is free of any non-monoester peroxy dicarboxylic acid or carboxylic acid with 10, 12, or more carbon atoms. Such non-ester 10, 12, or more carbon acids can impart undesirable residues (e.g., bad tasting and/or malodorous) to food product.

Each of the compositions listed above can be formulated by combining each of the listed ingredients. In addition, certain compositions including both acid and peroxy acid can be formulated by combining the acids and hydrogen peroxide, which forms peroxy acids. Typically, the pH of an equilibrium mixture is less than about 1 or about 2, and the pH of a 1% solution of the equilibrium mixture in water is about 2 to about 7, depending on the other components of the 1% solution, and the pH of a use solution can be from about 3 to about 7 depending on the other components.

Hydrogen Peroxide

The high concentration compositions of the invention typically also include a hydrogen peroxide constituent. Hydrogen peroxide in combination with the percarboxylic acid provides certain antimicrobial action against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible.

Many oxidizing agents can be used for generating peroxycarboxylic acids. Suitable oxidizing agents, in addition to hydrogen peroxide, include salts of perborate, percarbonate, and persulfate. Hydrogen peroxide is generally preferred for several reasons. After application of the $H_2O_2$/peroxycarboxylic acid germicidal agent, the residue left merely includes water and an acidic constituent. Deposition of these products on the surface of a food product processing apparatus, such as a bath or spray apparatus, will not adversely effect the apparatus, the handling or processing, or the food product washed therein.

Hydrogen peroxide ($H_2O_2$), has a molecular weight of 34.014 and it is a weakly acidic, clear, colorless liquid. The four atoms are covalently bonded in a H—O—O—H structure.

Generally, hydrogen peroxide has a melting point of −0.41° C., a boiling point of 150.2° C., a density at 25° C. of 1.4425 grams per cm$^3$, and a viscosity of 1.245 centipoise at 20° C.

Carrier

The high concentration composition of or employed in the method of the invention also includes a carrier. The carrier provides a medium which dissolves, suspends, or carries the other components of the high concentration composition. For example, the carrier can provide a medium for solubilization and production of peroxycarboxylic acid and for forming an equilibrium mixture. The carrier also functions to deliver and wet the high concentration composition of the invention to the food product. To this end, the carrier may contain any component or components that can facilitate these functions.

Polyols are also useful carriers, including polypropylene glycols, polyethylene glycols, sorbitol, and the like. Any of these compounds may be used singly or in combination with other organic or inorganic constituents or, in combination with water or in mixtures thereof.

Generally, the carrier makes up a large portion of the composition and may be the balance of the composition apart from the active antimicrobial components, adjuvants, and the like. Here again, the carrier concentration and type will depend upon the nature of the composition as a whole, the environmental storage, and method of application including concentration of the anti-microbial agent, among other factors. Notably the carrier should be chosen and used at a concentration which does not inhibit the antimicrobial efficacy of the active agent in the composition.

Adjuvants

The high concentration composition of or employed in the method of the invention can also include any number of adjuvants. Specifically, the composition can include stabilizing agents, wetting agents, hydrotropes or antimicrobial surfactants, thickeners, a surfactant, foaming agents, acidifiers, as well as pigments or dyes among any number of constituents which can be added to the composition. Such adjuvants can be preformulated with the high concentration composition or added to the system simultaneously, or even after, the addition of the high concentration composition. The composition can also contain any number of other constituents as necessitated by the application, which are known to those of skill in the art and which can facilitate the activity of the present invention.

Stabilizing Agents

Stabilizing agents can be added to the composition, for example, to stabilize the peracid and hydrogen peroxide and prevent the premature oxidation of this constituent within the composition.

Chelating agents or sequestrants generally useful as stabilizing agents in the present compositions include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid ($CH_3C(PO_3H_2)_2OH$) (HEDP), amino[tri(methylene phosphonic acid)]([$CH_2PO_3H_2$]$_2$(ethylene diamine[tetra methylene-phosphonic acid)], 2-phosphene butane-1,2,4-tricarboxylic acid, as well as the alkyl metal salts, ammonium salts, or alkyloyl amine salts, such as mono, di, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Amino phosphates and phosphonates are also suitable for use as chelating agents in the compositions and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2–4 carboxylic acid moieties and about 1–3 phosphonic acid groups. Such acids include 1-phosphono-1-methylsuccinic acid, phosphonosuccinic acid and 2-phosphonobutane-1,2,4-tricarboxylic acid.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), (N[CH2PO3H2]3), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in the present invention generally ranges from about 0.01 to about 10 wt-%, preferably from about 0.1 to about 5 wt-%, most preferably from about 0.5 to about 2 wt-%.

Wetting or Defoaming Agents

Also useful in the composition are wetting and defoaming agents. Wetting agents function to increase the surface contact or penetration activity of the high concentration composition. Wetting agents which can be used in the composition include any of those constituents known within the art to raise the surface activity of the composition.

Along these lines, surfactants, and especially nonionic surfactants, can also be useful in the present invention. Nonionic surfactants which can be useful in the present invention are those which include ethylene oxide moieties, propylene oxide moieties, as well mixtures thereof, and ethylene oxide-propylene oxide moieties in either heteric or block formation. Additionally useful in the present invention are nonionic surfactants which include an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties can be in any randomized or ordered pattern and of any specific length. Nonionic surfactants useful in the present invention can also include randomized sections of block and heteric ethylene oxide propylene oxide, or ethylene oxide-propylene oxide, such as ethylene diamine ethylene oxides, ethylene diamine propylene oxides, mixtures thereof, and ethylene diamine EO-PO compounds, including those sold under the tradename Tetronic.

Generally, the concentration of nonionic surfactant used in a composition of the present invention can range from about 0 wt-% to about 5 wt-% of the composition, preferably from about 0 wt-% to about 2 wt-% of the concentrate composition, and most preferably from about 0 wt-% to about 1 wt-% of the composition.

The composition can also contain additional ingredients as necessary to assist in defoaming. Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferably, are those antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Hydrotropes and Surfactants That Enhance Antimicrobial Activity

The food product wash composition of the invention or employed in the method of the invention can also include a hydrotrope coupler, a solubilizer, or an surfactant effective for enhancing antimicrobial performance. Such materials can be used to ensure that the composition remains phase stable and in a single highly active aqueous form, and that the compositional biocidal performance is improved over conventional peroxy carboxylic acid systems. Such hydrotrope solubilizers, couplers, or antimicrobial surfactants can be used at concentrations that maintain phase stability but do not result in unwanted compositional interaction.

Representative classes of hydrotrope solubilizers, coupling, or antimicrobial enhancing agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, an amine oxide, sugar esters (e.g., sorbitan esters), a $C_{8-10}$ alkyl glucoside, or mixtures thereof.

Preferred coupling agents and antimicrobial improving surfactants for use in the present compositions and methods include n-octane sulfonate and aromatic sulfonates such as an alkyl aryl sulfonate (e.g., sodium xylene sulfonate or naphthalene sulfonate). Many hydrotrope solubilizers independently exhibit some degree of antimicrobial activity at low pH. Such action adds to the efficacy of the invention but is not a primary criterion used in selecting an appropriate solubilizing agent. Since the presence of the peroxycarboxylic acid material in the protonated neutral state provides beneficial biocidal or antimicrobial activity, the coupling agent should be selected not for its independent antimicrobial activity but for its ability to provide effective single phase composition stability in the presence of substantially insoluble peroxycarboxylic acid materials and the more soluble compositions of the invention. Generally, any number of surfactants may be used consistent with the purpose of this constituent.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include β-N-alkylaminopropionic acids, n-alkyl- β-iminodipropionic acids, imidazoline carboxylates, n-alkyiletaines, amine oxides, sulfobetaines and sultaines.

Amine oxide surfactants useful with the invention include dioctyl methyl amine oxide, octyl dimethyl amine oxide, didecyl methyl amine oxide, decyl dimethyl amine oxide, lauryl dimethyl amine oxide, cocoa dimethyl amine oxide, and cocoamidopropyl dimethyl amine oxide.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer including an EO block and a PO block, a center block of polyoxypropylene units (PO), and having blocks of polyoxyethylene grated onto the polyoxypropylene unit or a center block of EO with attached PO blocks. Further, this surfactant can have further blocks of either polyoxyethylene or polyoxypropylene in the molecule. The average molecular weight of useful surfactants ranges from about 1000 to about 40,000 and the weight percent content of ethylene oxide ranges from about 10–80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula R—(EO)$_m$—(PO)$_n$ wherein m is an integer of about 2–10 and n is an integer from about 2–20. R can be any suitable radical such as a straight chain alkyl group having from about 6–20 carbon atoms.

Other useful nonionic surfactants include capped aliphatic alcohol alkoxylates. These end caps include but are not limited to methyl, ethyl, propyl, butyl, benzyl and chlorine. Useful alcohol alkoxylated include ethylene diamine ethylene oxides, ethylene diamine propylene oxides, mixtures thereof, and ethylene diamine EO-PO compounds, including those sold under the tradename Tetronic. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant is a fatty acid alkoxylate wherein the surfactant includes a fatty acid moiety with an ester group including a block of EO, a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Thickening or Gelling Agents

Thickeners useful in the present invention include those which do not leave contaminating residue on the surface of food product or food product processing apparatus. That is, preferred thickeners or gelling agents do not include components incompatible with food or other sensitive products in contact areas.

Generally, thickeners which may be used in the present invention include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

Formulation

The compositions of or used in the methods of the invention can be formulated by combining the antimicrobially active materials (e.g., aliphatic carboxylic mono- or di-esters, and hydrogen peroxide) with adjuvant or other components with the materials that form the high concentration composition. The compositions can also be formulated with preformed peroxycarboxylic acids. The preferred compositions of the invention can be made by mixing the aliphatic carboxylic mono- or di-esters or mixture thereof with an optional hydrotrope solubilizer or coupler, reacting the mixture with hydrogen peroxide and then adding the balance of required ingredients to provide rinsing and antimicrobial action.

A stable equilibrium mixture is produced containing the carboxylic acid or blend with hydrogen peroxide and allowing the mixture to stand for 1–21 days at 15° C. or more. With this preparatory method, an equilibrium mixture will be formed containing an amount of hydrogen peroxide, unoxidized acid, oxidized or peroxycarboxylic acid and unmodified couplers, solubilizer, or stabilizers.

Use Solutions

The invention contemplates a concentrate composition which is diluted to a use solution prior to application to an object. Primarily for reasons of economics, the concentrate would normally be marketed and an end user would preferably dilute the concentrate with water or an aqueous diluent to a use solution.

The level of active components in the concentrate composition is dependent on the intended dilution factor and the desired activity of the peroxycarboxylic acid compound and the carboxylic acid. Generally, a dilution of about 0.2 to about 50 fluid ounces, more preferably 1 to 30 fluid ounces, most preferably about 4 to about 30 fluid ounces to about 100 gallons of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

Methods Employing the High Concentration Monoester Peroxy Dicarboxylic Acid Compositions The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps and pre- or post-surgical scrubs.

The antimicrobial compositions can also be used in veterinary products such as mammalian skin treatments or in products for sanitizing or disinfecting animal enclosures, pens, watering stations, and veterinary treatment areas such as inspection tables and operation rooms.

The present compositions can be employed for reducing the population of pathogenic microorganisms, such as pathogens of humans, animals, and the like. The compositions can exhibit activity against pathogens including fungi, molds, bacteria, spores, and viruses, for example, parvovirus, coxsackie virus, herpes virus, S. aureus, E. coli, Streptococci, Legionella, mycobacteria, or the like. Such pathogens can cause a varieties of diseases and disorders, including athletes foot, hairy hoof wart disease, Mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The present composition is useful in the cleaning or sanitizing of containers, processing facilities, or equipment in the food service or food processing industries. The antimicrobial compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The antimicrobial compositions can also be used on or in other industrial equipment and in other hunstrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as Legionella.

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant sanitizing composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, more preferably about 30 to about 120 seconds. The present sanitizing composition is found to remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities includes the following steps. The use solution of the invention is introduced into the process facilities at a temperature in the range of about 4° C. to 60° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition is preferably circulated through the process facilities for 10 minutes or less.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use solution is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a composition of the present invention can be applied to or brought into contact with an object by any conventional method or apparatus for applying an antimicrobial or cleaning composition to an object. For example, the object can be wiped with, sprayed with, and/or immersed in the composition, or a use solution made from the composition. The composition can be sprayed or wiped onto a surface; the composition can be caused to flow over the surface, or the surface can be dipped into the composition. Contacting can be manual or by machine.

The compositions can be formulated as liquids, gels, aerosols, waxes, solids, or powders. If steam or another gaseous diluting solvent is employed, then the compositions can be formulated to be applied in a gaseous state.

Contacting a Food Product with the High concentration Monoester Peroxy Dicarboxylic Acid Compositions The present method and system provide for contacting a food product with a high concentration composition, or a use solution made from a high concentration composition, employing any method or apparatus suitable for applying such a composition. For example, the method and system of the invention can contact the food product with a spray of the use solution, by immersion in the use solution, by foam or gel treating with the use solution, or the like. Contact with a spray, a foam, a gel, or by immersion can be accomplished by a variety of methods known to those of skill in the art for applying antimicrobial agents to food. These same methods can also be adapted to apply the high concentration compositions, or use solutions, of the invention to other objects.

The present methods require a certain minimal contact time of the composition with food product for occurrence of significant antimicrobial effect. The contact time can vary with concentration of the use solution, method of applying the use solution, temperature of the use solution, amount of soil on the food product, number of microorganisms on the food product, type of antimicrobial agent, or the like. Preferably the exposure time is at least about 5 to about 15 seconds.

A preferred method for washing food product employs a pressure spray including the composition. During application of the spray solution on the food product, the surface of the food product can be moved with mechanical action, preferably agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., preferably about 20 to 60° C. to increase efficacy. The spray composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One preferred automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the high concentration compositions of the invention. These steam jets can be used in combination with cooling water to ensure that the treatment reaching the food product surface is less than 65° C., preferably less than 60° C. The temperature of the spray on the food product is important to ensure that the food product is not substantially altered (cooked) by the temperature of the spray. The spray pattern can be virtually any useful spray pattern.

Immersing a food product in a liquid composition according to the present invention can be accomplished by any of a variety of methods known to those of skill in the art. For example, the food product can be placed into a tank or bath containing the composition. Alternatively, the food product can be transported or processed in a flume of the present use solution. The washing solution is preferably agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the present composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

EXAMPLES

Inventive compositions including certain anionic or amine oxide surfactants exhibit improved economics and microbial reduction profile compared to compositions lacking these surfactants. The following Examples compare results obtained with certain surfactant blends, which improve antimicrobial efficacy compared to conventional formulations lacking these certain surfactants. In particular, the Examples compare the present compositions to conventional compositions described in PCT patent publication WO 9828267(A1) and commercial available conventional monoester peroxy dicarboxylic acid blends sold under the tradename Perestane™ by SOLVAY S. A. (Belgium).

Example 1

Surfactant Increases Concentration of Monoester Peroxy Dicarboxylic Acid Antimicrobial Agents Certain surfactants and certain levels of surfactants were employed in monoester peroxy dicarboxylic acid antimicrobial compositions to determine whether these surfactants increased the concentration and antimicrobial activity of the antimicrobial agent in these compositions.

Materials and Methods

Compositions were formulated according to Table 1 below and tested for antimicrobial activity by known methods. The equilibrium concentrations and costs were calculated according from information known to those of skill in the art and described in notes under Table 1.

Results

The results in Table 1 show the advantage of generating a high concentration monoester peroxy dicarboxylic acid composition according to the present invention and including certain surfactants. The present compositions exhibit, compared to the conventional formulations, a higher yield of monoester peroxy dicarboxylic acid, a higher level of available oxygen, greater antimicrobial activity, and a lower cost. This increased activity is achieved at a lower concentration of monoester peroxy dicarboxylic acid. These advantages result from the selection of surfactant.

TABLE 1

Comparison of Concentration, Cost and Efficacy for Conventional Formulations and the Present Compositions.

| Raw Materials | Conventional Formulation[1] ~4–6% Monoester Dicarboxylic Peracid | | Compositions of the Present Invention 7–22% Monoester Dicarboxylic Peracid with Surfactants | |
|---|---|---|---|---|
| | start amount | equilibrium yield | start amount | equilibrium active yield |
| DBE-5[2] | 20.0–32.0 | 16.8–23.6 | 24.0–45.0 | 18.0–41.6 |
| $H_2O_2$ (35%) | 44.0–52.4 | 13.6–14.1 | 0.0–52.4 | 0.0–14.1 |
| $H_2O_2$ (50%) | 0.0–0.0 | 0.0–0.0 | 0.0–45.0 | 0.0–15.8 |
| HEDP[3] (60%) | 0.6–2.6 | 0.6–2.6 | 0.6–2.6 | 0.6–2.6 |
| Water (added or from raw materials) | 5.0–25.4 | 42.3–56.0 | 0.0–15.0 | 17.1–47.3 |
| Methanol | 3.0–8.0 | 4.0–8.0 | 7.0 | 8.0 |
| sulfuric acid | 0.5–1.5 | 0.5–1.5 | 1.0 | 1.0 |
| LAS acid (98%)[4] | 0.0–1.0 | 0.0–1.0 | 2.5–22.0 | 2.5–22.0 |
| Amine Oxide[5] | 0.0–1.0 | 0.0–1.0 | 2.5–22.0 | 2.5–22.0 |
| secondary alcohol ethoxylate (9-EO) | 0.0–5.0 | 0.0–5.0 | 0.0–22.0 | 0.0–22.0 |
| DBE peracid yield[6] | ~4–6% | | ~7–22% | |
| Available Oxygen[7] | 5–7 | | 6–11 | |
| Microbial Reduction[8] (120 ppm peracid) | 2.7[9] | | 6.7[10] | |
| Microbial Reduction Use Requirement[11] (7-day Ready to Use) | 180 ppm | | ≦120 ppm | |
| 7-day use cost[12] (% of conventional quaternary ammonium antimicrobial compositions) | +212% to +39% | | +20% to 0% | |

[1]WO 9828267(A1)
[2]DBE-5 dibasic diesters from DuPont Nylon Intermediates and Specialties; Wilmington, DE.
[3]1-hydroxyethylidene–1,1-diphosphonic acid
[4]Dodecylbenzene sulfonic acid
[5]A C8–16 alkyl or dialkyl amine oxide.
[6]The equilibrium yield of titrateable peracids
[7]Based on the equilibrium yields of peracids and hydrogen peroxide.
[8]Microbial reduction of S. aureus in 30 seconds at 25° C. at a titrateable concentration of 120 ppm peracid.
[9]A peracid concentrate using an ethylene oxide/propylene oxide copolymer according to WO 9828267(A1).
[10]A peracid concentrate using 3.0 wt-% dodecylbenzene sulfonic acid along with the nonionic described in Table 1.
[11]The minimal peracid titrateable level to allow for >5-log micro reduction of S. choleraesuis, P. aeruginosa, and S. aureus over the seven day use test; allowing for equilibrium shifts.
[12]Use cost based on the comparable quaternary ammonium chloride use-gallon raw material cost.

Conclusions

Employing certain surfactants and amounts of surfactants in compositions of monoester peroxy dicarboxylic acid compositions increases the concentrations of these antimicrobial agents that can be achieved. This decreases the cost of use.

Example 2

Surfactant Improves Activity of Monoester Peroxy Dicarboxylic Acid Compositions as Disinfectants Certain surfactants and certain levels of surfactants were employed in monoester peroxy dicarboxylic acid antimicrobial compositions to determine whether these surfactants increased the antimicrobial activity of these compositions when tested as disinfectants.

Materials and Methods

Compositions were formulated according to Table 2 below and tested for antimicrobial activity by known methods for evaluating hospital disinfectants. Briefly, this hospital disinfectant test evaluates the composition against the test organism $S.$ $aureus$ in a carrier test. Passing this hospital disinfectant test requires $\leq 1$ positive tube out of 40 after being diluted into 500 ppm synthetic hard water at 20° C. In these Examples ppm of Perestane refers to titrateable peroxycarboxylic acid.

Results

The results in Table 2 show the advantage of employing certain surfactants according to the present invention. The present compositions pass the disinfectant test at peroxycarboxylic acid concentrations of only 42 ppm with anionic. The conventional (Perestane™) formulations passed only at levels more than 4-times higher (180 ppm). Increased effectiveness as a disinfectant results from the selection of surfactant.

TABLE 2

The Present Compositions are Active as Disinfectants

| Monoester Peroxy Dicarboxylic Acid | LAS[1] (ppm) | NAS[2] (ppm) | Octanoic Acid (ppm) | Microbial Reduction[5] |
|---|---|---|---|---|
| Conventional Formulations ||||| 
| 1 Perestane[3] - 90 ppm | 0 ppm | 0 ppm | 0 ppm | failed |
| 2 Perestane[3] - 150 ppm | 0 ppm | 0 ppm | 0 ppm | failed |
| 3 Perestane[3] - 180 ppm | 0 ppm | 0 ppm | 0 ppm | passed |
| Compositions of the Present Invention |||||
| 4 Perestane ™[3] (63 ppm) plus octanoic acid | 0 ppm | 0 ppm | 40 ppm | passed |
| 5 Perestane ™[3] (42 ppm) plus octanoic acid | 0 ppm | 0 ppm | 40 ppm | failed |
| 6 Perestane ™[3] (42 ppm) plus surfactant[4] | 0 ppm | 80 ppm | 0 ppm | passed |
| 7 Perestane ™[3] (42 ppm) plus surfactant[4] | 80 ppm | 0 ppm | 40 ppm | passed |
| 8 Perestane ™[3] (442 ppm) plus surfactant[4] | 40 ppm | 0 ppm | 40 ppm | passed |
| 9 Perestane ™[3] (42 ppm) plus surfactant[4] | 40 ppm | 40 ppm | 40 ppm | passed |
| 10 Perestane ™[3] (21 ppm) plus surfactant[4] | 0 ppm | 0 ppm | 40 ppm | failed |

[1]Dodecyl benzene sulfonic acid
[2]A secondary alcohol ethoxylate (9-ethylene oxide units).
[3]Perestane ™ includes a mixture of monomethylester monoperoxydicarboxylic glutaric, succinic and adipic acids and hydrogen peroxide and water.
[4]An in situ combination of the commercial Perestane ™ and the noted surfactants just prior to biocidal testing.
[5]pH = 3 with 200 ppm citric acid.

Conclusions

Employing certain surfactants and amounts of surfactants in compositions of monoester peroxy dicarboxylic acid compositions provides effective disinfectants.

Example 3

Surfactant Improves Activity of Monoester Peroxy Dicarboxylic Acid Compositions as a Food Contact Sanitizer Certain surfactants and certain levels of surfactants were employed in monoester peroxy dicarboxylic acid antimicrobial compositions to determine whether these surfactants increased the antimicrobial activity of these compositions when tested as food contact sanitizers.

Materials and Methods

Compositions were formulated according to Table 3 below and tested for antimicrobial activity by known methods for evaluating food contact sanitizers. Briefly, the food sanitizer test evaluates the composition against two test organisms, $S.$ $aureus$ and $E.$ $coli$. Passing this food sanitizer test requires a 5-log reduction in 30 seconds at 20° C. for these two organisms.

Results

The results in Table 3 show the advantage of employing certain surfactants according to the present invention. The data shows that the conventional compositions are effective against one organism ($E.$ $coli$), but much less effective against $S.$ $aureus$; except at high concentrations. The current anionic surfactant compositions are effective against both organisms, even at low concentrations of peracids. The present compositions pass the food contact sanitizer test at peroxycarboxylic acid concentrations of only 59 ppm with anionic surfactant. The conventional (Perestane™) formulations passed only at levels of 180 ppm. Increased effectiveness as a food contact sanitizer results from the selection of surfactant.

TABLE 3

The Present Compositions are Active as Food Contact Sanitizers

| Monoester Peroxy Dicarboxylic Acid | LAS[1] (ppm) | Nonionic Surfactant (ppm) | 30 Second Microbial Log Reduction[2] | |
|---|---|---|---|---|
| | | | S. aureus | E. coli |
| Conventional Formulations | | | | |
| Perestane ™[3] - | | | | |
| 1  100 ppm | 0 ppm | 0 ppm | 0.5 | >7.4 |
| 2  140 ppm | 0 ppm | 0 ppm | 3.4 | >7.4 |
| 3  180 ppm | 0 ppm | 0 ppm | >7.0 | >7.0 |
| Compositions of the Present Invention | | | | |
| 4  Perestane ™[4] - 140 ppm | 166 ppm | 166 ppm[5] | 6.5 | >7.4 |
| 5  Perestane ™[4] - 140 ppm | 10 ppm | 90 ppm[6] | >7.9 | >7.4 |
| 6  Perestane ™[4] - 100 ppm | 33 ppm | 100 ppm[6] | >7.9 | >7.4 |
| 7  140 ppm | 33 ppm | 100 ppm | >7.9 | >7.4 |

[1]Dodecylbenzene sulfonic acid
[2]Buffered to pH = 3.
[3]Perestane ™ includes a mixture of hydrogen peroxide and monomethyl esters of monoperoxy glutaric, succinic and adipic acids.
[4]A secondary alcohol ethoxylate (9 EO).
[5]Pluronic F108; BASF
[6]Pluronic L61, BASF

Conclusions

Employing certain surfactants and amounts of surfactants in compositions of monoester peroxy dicarboxylic acid compositions provides food contact sanitizers.

Example 4

Selected Surfactants Increased Antimicrobial Rate of Kill by Monoester Peroxy Dicarboxylic Acid Compositions Certain surfactants and certain levels of surfactants were employed in monoester peroxy dicarboxylic acid antimicrobial compositions to determine whether these surfactants increased the rate of kill by these compositions when tested as food contact sanitizers.

Materials and Methods

Compositions were formulated according to Table 4 below and tested for antimicrobial activity by known methods for evaluating food contact sanitizers, as described above in Example 5, but employing only *S. aureus* as test organism.

Results

The results in Table 4 show the advantage of employing certain surfactants according to the present invention. The present compositions pass the food contact sanitizer test at peroxycarboxylic acid concentrations of only 70–120 ppm with anionic or amine oxide surfactants. The conventional (Perestane™) formulations passed only at levels of 180 ppm. Increased effectiveness as a food contact sanitizer results from the selection of surfactant.

TABLE 4

The Present Compositions are Active as Food Contact Sanitizers

| Monoester Peroxy Dicarboxylic Acid | LAS[1] (ppm) | AO-12[2] (ppm) | Nonionic Surfactant (ppm) | 30 second Microbial Log Reduction of S. aureus |
|---|---|---|---|---|
| Conventional Formulations | | | | |
| Perestane ™[5] | | | | |
| 1   90 ppm | 0 ppm | 0 ppm | 0 ppm | 1.0 |
| 2  120 ppm | 0 ppm | 0 ppm | 0 ppm | 2.4 |
| 3  150 ppm | 0 ppm | 0 ppm | 0 ppm | 4.5 |
| 4  180 ppm | 0 ppm | 0 ppm | 0 ppm | >7.0 |
| Perestane ™[5] | | | | |
| 5   70 ppm | 0 ppm | 0 ppm | 50 ppm[3] | 0.7 |
| 6   90 ppm | 0 ppm | 0 ppm | 64 ppm[3] | 1.2 |
| 7  120 ppm | 0 ppm | 0 ppm | 86 ppm[3] | 2.7 |
| Compositions of the Present Invention | | | | |
| Perestane ™ | | | | |
| 8  120 ppm | 43 ppm | 0 ppm | 43 ppm[4] | 7.0 |
| 9  150 ppm | 54 ppm | 0 ppm | 54 ppm[4] | 6.6 |
| 10 180 ppm | 64 ppm | 0 ppm | 64 ppm[4] | 6.1 |
| 11 Perestane ™ 120 ppm | 21 ppm | 0 ppm | 21 ppm[4] | >7.0 |
| Perestane ™[5] | | | | |
| 12  70 ppm | 50 ppm | 0 ppm | 50 ppm[3] | 5.7 |
| 13  90 ppm | 54 ppm | 0 ppm | 64 ppm[3] | 6.2 |
| 14 120 ppm | 64 ppm | 0 ppm | 86 ppm[3] | 6.7 |
| Perestane ™ | | | | |
| 15 120 ppm | 0 ppm | 21 ppm | 0 ppm | 6.2 |
| 16 150 ppm | 0 ppm | 27 ppm | 0 ppm | 6.7 |
| 17 180 ppm | 0 ppm | 32 ppm | 0 ppm | >7.0 |
| Perestane ™[5] | | | | |
| 18  50 ppm | 0 ppm | 36 ppm | 0 ppm | 2.1 |
| 19  75 ppm | 0 ppm | 54 ppm | 0 ppm | 3.2 |
| 20 100 ppm | 0 ppm | 72 ppm | 0 ppm | 6.8 |
| 21 120 ppm | 0 ppm | 43 ppm | 0 ppm | >7.0 |
| 22 150 ppm | 0 ppm | 54 ppm | 0 ppm | 5.3 |
| 23 180 ppm | 0 ppm | 64 ppm | 0 ppm | >7.0 |
| Perestane ™ | | | | |
| 24 120 ppm | 0 ppm | 43 ppm | 43 ppm[4] | >7.0 |
| 25 150 ppm | 0 ppm | 54 ppm | 54 ppm[4] | 5.8 |
| 26 180 ppm | 0 ppm | 64 ppm | 64 ppm[4] | 7.0 |
| 24 Perestane ™ 120 ppm | 0 ppm | 21 ppm | 43 ppm[4] | 7.0 |

[1]Dodecylbenzene sulfonic acid
[2]Cocoa-dimethyl amine oxide
[3]Pluronic F108
[4]A secondary alcohol ethoxylate (9 EO).
[5]Perestane ™ includes a mixture of hydrogen peroxide and monomethyl esters of monoperoxy glutaric, succinic and adipic acids.

Conclusions

Employing certain surfactants and amounts of surfactants in compositions of monoester peroxy dicarboxylic acid compositions provides effective food contact sanitizers.

Example 5

Selected Surfactants Increased Antimicrobial Activity of Monoester Peroxy Dicarboxylic Acid Compositions in Laundry and Warewashing Applications Certain surfactants and certain levels of surfactants were employed in monoester peroxy dicarboxylic acid antimicrobial compositions to determine whether these surfactants improves antimicrobial activity of these compositions when tested in laundry and warewashing applications.

Materials and Methods

Compositions were formulated according to Table 5 below and tested for antimicrobial activity by methods similar to those employed in Examples 3 and 4, but at the elevated temperature of 120° C. This high temperature models laundry washing and warewashing conditions.

Results

The results in Table 5 show the advantage of employing certain surfactants according to the present invention. The present compositions cause about or more than a 7-log reduction in microorganism population at peroxycarboxylic acid concentrations of only 50 ppm with anionic or amine oxide surfactant. The conventional (Perestane™) formulations provided only less than or equal to 2.6-log reductions in populations of microorganism at concentrations up to 120 ppm. Increased effectiveness at high temperatures results from the selection of surfactant.

TABLE 5

Improved Antimicrobial Activity at 120° C. With Selected Surfactants

| Monoester Peroxy Dicarboxylic Acid | LAS[1] (ppm) | AO-12[2] (ppm) | Nonionic Surfactant (ppm) | 120° C. 30 second Microbial Log Reduction[3] of S. aureus |
|---|---|---|---|---|
| Conventional Formulations ||||| 
| Perestane ™[4] |||||
| 1  70 ppm | 0 ppm | 0 ppm | 0 ppm | 0.6 |
| 2  90 ppm | 0 ppm | 0 ppm | 0 ppm | 1.0 |
| 3  120 ppm | 0 ppm | 0 ppm | 0 ppm | 2.6 |
| Compositions of the Present Invention |||||
| Perestane ™[4] |||||
| 4  50 ppm | 0 ppm | 36 ppm | 0 ppm | >7.0 |
| 5  75 ppm | 0 ppm | 54 ppm | 0 ppm | 6.7 |
| 6  100 ppm | 0 ppm | 71 ppm | 0 ppm | 7.0 |
| 7  120 ppm | 0 ppm | 85 ppm | 0 ppm | 7.0 |
| Perestane ™[4] |||||
| 11  50 ppm | 36 ppm | 0 ppm | 36 ppm[5] | >7.0 |
| 12  70 ppm | 54 ppm | 0 ppm | 54 ppm[5] | >7.0 |
| 13  100 ppm | 71 ppm | 0 ppm | 71 ppm[5] | >7.0 |
| 14  120 ppm | 85 ppm | 0 ppm | 85 ppm[5] | >7.0 |

[1]Dodecylbenzene sulfonic acid
[2]Cocoa-dimethyl amine oxide
[3]pH = 3.
[4]Perestane ™ includes a mixture of hydrogen peroxide and monomethyl esters of monoperoxy glutaric, succinic and adipic acids.
[5]A secondary alcohol ethoxylate (9 EO).

Conclusions

Employing certain surfactants and amounts of surfactants in compositions of monoester peroxy dicarboxylic acid compositions provides improved activity against microorganisms at the high temperatures typically employed for laundry washing and ware washing.

Example 6

Selected Surfactants Increased Antimicrobial Activity of Monoester Peroxy Dicarboxylic Acid Compositions Against Microorganisms That Cause Tuberculosis Certain surfactants and certain levels of surfactants were employed in monoester peroxy dicarboxylic acid antimicrobial compositions to determine whether these surfactants improves antimicrobial improved activity of these compositions against Mycobacteria, which cause *tuberculosis*.

Materials and Methods

Compositions were formulated according to Table 6 below and tested for against Mycobacteria according to methods known to those of skill in the art. Briefly, the compositions were tested against a Tuberculocidal screening organism, *M bovis* BCG. Passing the antituberulcidal test required a 5-log reduction in microorganism population in 10 minutes at 20° C.

Results

The results in Table 6 show the advantage of employing certain surfactants according to the present invention. The present compositions pass the food contact sanitizer test at peroxycarboxylic acid concentrations of only 42 ppm with anionic surfactant. The conventional (Perestane™) formulations failed the test at concentrations of 2400 to 6700 ppm. Increased effectiveness against Tuberculocidal organisms results from the selection of surfactant.

Substantial biocidal improvements, over conventional formulations, are found using the present compositions employing an anionic surfactant; cf., experiments 1–3 versus 4–5, 8–11. The data also demonstrates the possibility of over coupling an antimicrobial system by the use of excess anionic surfactant; e.g., experiment 12.

TABLE 6

Improved Tuberculocidal Formulations Employing Selected Surfactants

| Monoester Peroxy Dicarboxylic Acid | Octanoic Acid (ppm) | LAS[1] (ppm) | M. bovis-BCG Log Reduction | | |
|---|---|---|---|---|---|
|  |  |  | 5 min | 10 min | 20 min |
| Controls ||||||
| 1 Perestane ™[2] (2434 ppm) | 0 | 0 | 0.3 | 0.3 | 0.3 |
| 2 Perestane ™[2] (4614 ppm) | 0 | 0 | 0.2 | 0.2 | 2.2 |
| 3 Perestane ™[2] (6736 ppm) | 0 | 0 | 0.3 | 1.8 | 4.0 |
| Compositions of the Present Invention ||||||
| 4 Perestane ™[3] 21 ppm | 500 | 1000 | — | — | 5.0 |
| 5 Perestane ™[3] 42 ppm | 1000 | 1000 | >6.4 | >6.4 | >6.4 |
| 6 Perestane ™[3] 42 ppm | 1000 | 0 | <0.5 | <0.5 | <0.5 |
| 7 Perestane ™[3] 126 ppm | 1000 | 0 | <0.5 | <0.5 | <0.5 |
| 8 Perestane ™[3] 126 ppm | 1000 | 1000 | >6.4 | >6.4 | >6.4 |
| 9 Perestane ™[3] 531 ppm | 0 | 500 | 1.0 | 0.9 | 1.2 |
| 10 Perestane ™[3] 531 ppm | 500 | 0 | >6.4 | >6.4 | >6.4 |
| 11 Perestane ™[3] 531 ppm | 500 | 500 | 3.9 | 5.8 | >6.4 |
| 12 Perestane ™[3] 531 ppm | 100 | 1000 | 0.1 | 0.1 | 0.5 |
| 13 Perestane ™[3] 531 ppm | 0 | 250 | 0.0 | 0.0 | 0.0 |

[1]Dodecylbenzene sulfonic acid.
[2]Perestane ™ includes a mixture of hydrogen peroxide and monomethyl esters of monoperoxy glutaric, succinic and adipic acids.

Conclusions

Employing certain surfactants and amounts of surfactants in compositions of monoester peroxy dicarboxylic acid compositions provides improved activity against microorganisms that cause *tuberculosis*.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A high concentration monoester peroxy dicarboxylic acid composition comprising:
    more than 6 wt-% monoester peroxy dicarboxylic acid;
    at least about 10 wt-% diester dicarboxylate;
    about 0.1 wt-% to about 25 wt-% anionic surfactant, amine oxide surfactant, or a mixture thereof;
    at least about 4 wt-% hydrogen peroxide; and
    about 8 to about 55 wt-% total water.

2. The composition of claim 1, comprising at least about 7 wt-% monoester peroxy dicarboxylic acid.

3. The composition of claim 1, comprising at least about 15 wt-% diester dicarboxylate.

4. The composition of claim 1, comprising at least about 8 wt-% hydrogen peroxide.

5. The composition of claim 1, comprising about 8 to about 35 wt-% total water.

6. The composition of claim 1, wherein the anionic surfactant comprises alkylbenzene sulfonic acid, alkylbenzene sulfonate salt, or a mixture thereof.

7. The composition of claim 6, wherein the anionic surfactant comprises dodecylbenzene sulfonic acid or a salt thereof.

8. The composition of claim 1, wherein the amine oxide surfactant comprises alkyl dimethyl amine oxide, dialkyl methyl amine oxide, or a mixture thereof.

9. The composition of claim 1, wherein the surfactant further comprises nonionic surfactant.

10. The composition of claim 1, further comprising 0 to about 30 wt-% inert organic solvent.

11. The composition of claim 10, wherein the inert organic solvent comprises a diester of malonic acid, a diester of adipic acid, a diester of glutaric acid, a diester of succinic acid, a diester of sebacic acid, benzyl alcohol, or mixtures thereof.

12. A high concentration diester dicarboxylate-peroxide composition comprising:
    at least about 15 wt-% diester dicarboxylate;
    about 0.1 wt-% to about 25 wt-% anionic surfactant, amine oxide surfactant, or a mixture thereof;
    at least about 10 wt-% hydrogen peroxide; and
    less than about 30 wt-% total water.

13. The composition of claim 12, comprising at least about 20 wt-% diester carboxylate.

14. The composition of claim 12, comprising at least about 14 wt-% hydrogen peroxide.

15. The composition of claim 12, comprising less than about 25 wt-% total water.

16. The composition of claim 12, further comprising 0 to about 30 wt-% inert organic solvent.

17. An antimicrobial use solution comprising:
    from about 5 ppm to about 35,000 ppm monoester peroxy dicarboxylic acid;
    from about 2 ppm to about 1,500 ppm anionic surfactant, from about 2 ppm to about 1500 ppm amine oxide surfactant, or a mixture thereof; and
    carrier.

18. The use solution of claim 17, comprising about 20 ppm to about 7000 ppm monoester peroxy dicarboxylic acid and about 20 ppm to about 800 anionic surfactant.

19. The use solution of claim 17, comprising about 40 ppm to about 2000 ppm monoester peroxy dicarboxylic acid and about 40 ppm to about 400 ppm anionic surfactant.

20. The use solution of claim 17, comprising about 40 ppm to about 400 ppm monoester peroxy dicarboxylic acid and about 40 ppm to about 200 ppm anionic surfactant.

21. The use solution of claim 17, comprising:
    about 5 ppm to about 180 ppm monoester peroxy dicarboxylic acid; and
    about 10 ppm to about 240 ppm anionic surfactant, about 10 ppm to about 240 ppm amine oxide surfactant, or a mixture thereof.

22. The use solution of claim 17, comprising:
    about 5 ppm to about 180 ppm monoester peroxy dicarboxylic acid; and
    about 10 ppm to about 140 ppm anionic surfactant, about 10 ppm to about 140 ppm amine oxide surfactant, or a mixture thereof.

23. The use solution of claim 17, comprising:
    about 5 ppm to about 120 ppm monoester peroxy dicarboxylic acid; and
    about 10 ppm to about 120 ppm anionic surfactant, about 10 ppm to about 120 ppm amine oxide surfactant, or a mixture thereof.

24. The use solution of claim 17, comprising about 130 ppm to about 600 ppm monoester peroxy dicarboxylic acid and about 2 ppm to about 1000 ppm anionic surfactant, and further comprising about 40 ppm to about 1000 ppm fatty acid.

25. A method of reducing population of microorganism on an object, comprising:
    contacting the object with use solution of a high concentration monoester peroxy dicarboxylic acid composition; the high concentration composition comprising:
    more than 6 wt-% mono-monoester peroxy dicarboxylic acid;
    at least about 10 wt-% diester dicarboxylate;
    about 0.1 wt-% to about 25 wt-% anionic surfactant, amine oxide surfactant, or a mixture thereof;
    at least about 4 wt-% hydrogen peroxide; and
    about 8 to about 55 wt-% total water.

26. The method of claim 25, wherein the object comprises a food product, a food processing surface, a health care surface, a plant product, a body or stream of water, a body or stream of gas, a hospitality sector surface, an industrial sector surface, an agricultural surface, a veterinary surface, or a combination thereof.

27. The method of claim 25, herein the object comprises a hard surface.

28. The method of claim 25, wherein the object comprises an air stream.

29. The method of claim 25, wherein the object comprises an elastomer, a plastic, a woven substrate, a non-woven substrate, or a combination thereof.

30. The method of claim 25, wherein contacting comprises spraying the composition, immersing the object in the composition, foam or gel treating the object with the composition, or a combination thereof.

31. The method of claim 25, further comprising:
diluting the high concentration monoester peroxy dicarboxylic acid composition by about 1:10,000 to about 1:1 with a diluent to form the use solution.

32. The method of claim 31, comprising diluting with water.

33. A method of making a high concentration equilibrium mono-monoester peroxy dicarboxylic acid composition comprising:
formulating
diester dicarboxylate,
hydrogen peroxide, and
water;
to achieve concentrations of:
at least about 15 wt-% diester dicarboxylate;
about 0.1 wt-% to about 25 wt-% anionic surfactant, amine oxide surfactant, or a mixture thereof;
at least about 10 wt-% hydrogen peroxide; and
less than about 40 wt-% total water;
equilibrating the formulation;
thereby making the high concentration equilibrium mono-monoester peroxy dicarboxylic acid composition.

* * * * *